Figure 1:
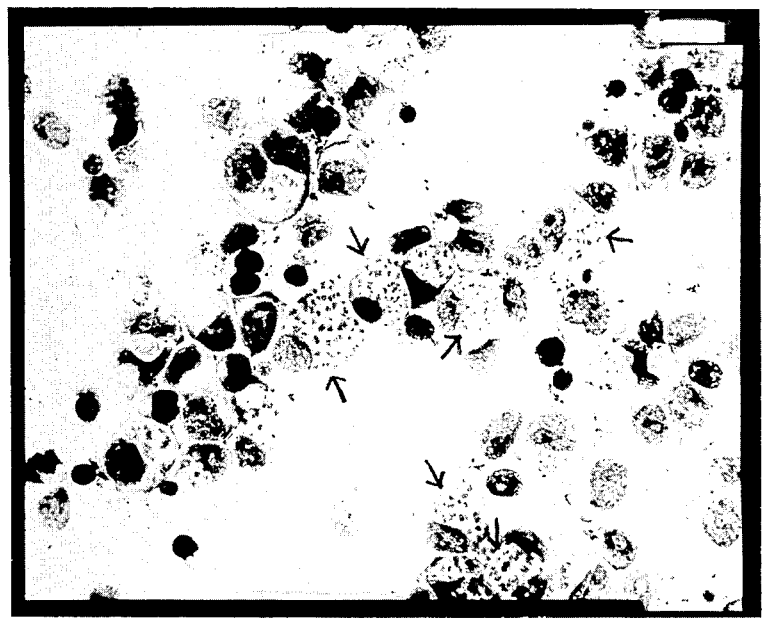
Figure 2:

United States Patent [19]

Wright

[11] Patent Number: 4,824,666
[45] Date of Patent: Apr. 25, 1989

[54] METHOD OF LARGE SCALE GROWTH OF TOXOPLASMIC MICROORGANISMS

[75] Inventor: D. Craig Wright, Gaithersburg, Md.

[73] Assignee: The United States of America as represented by the Secretary of the Army, Washington, D.C.

[21] Appl. No.: 120,041

[22] Filed: Nov. 13, 1987

[51] Int. Cl.$^4$ .................... A61K 39/002; G01N 33/54
[52] U.S. Cl. ........................................ 424/88; 424/1.1; 424/93; 435/252.1; 436/536
[58] Field of Search ........................... 424/88, 93, 1.1; 435/253; 436/536

[56] References Cited

U.S. PATENT DOCUMENTS

| | | | |
|---|---|---|---|
| 4,473,548 | 9/1984 | Frenkel et al. | 424/88 |
| 4,473,549 | 9/1984 | Frenkel et al. | 424/88 |
| 4,480,043 | 10/1984 | Trouyez | 436/536 |
| 4,564,592 | 1/1986 | Gaafar et al. | 435/68 |

FOREIGN PATENT DOCUMENTS 0100710  2/1984  European Pat. Off. .............. 424/88

OTHER PUBLICATIONS

ATCC, Catalogue of Cell Lines & Hybridomas, ATCC CRL 1593, U-937 (Human histiocytic lymphoma), p. 139, 5th edition, 1985.

Primary Examiner—Howard E. Schain
Attorney, Agent, or Firm—Francis A. Cooch; Paul E. O'Donnell, Jr.; Werten F. W. Bellamy

[57] ABSTRACT

A method of producing large scale growth of parasites of the genus Toxoplasma is disclosed which comprises inoculating the microorganisms into a non-adherent human cell line, such as a monocytoid lymphoma cell line, and maintaining the cell line in tissue culture media capable of supporting the growth of the microorganism while the cell line is being maintained. This large scale production allows for the development of vaccines for Toxoplasma microorganisms which previously have been hard to grow in the numbers needed to readily prepare vaccines, and allows for more rapid antibody detection procedures with regard to these microorganisms. There are also disclosed methods for preparing such vaccines, and methods for carrying out antibody detection assays.

7 Claims, 2 Drawing Sheets

METHOD OF LARGE SCALE GROWTH OF TOXOPLASMIC MICROORGANISMS

FIELD OF THE INVENTION

The invention relates to a method of large scale production of *Toxoplasma gondii* for use in vaccines and rapid antibody detection.

BACKGROUND OF THE INVENTION

*Toxoplasma gondii* is a frequent cause of disease in humans and animals. It is very often a cause of central nervous system infection in patients with the acquired immune deficiency syndrome (up to 25%), causes retinitis and blindness in children and adults and congenital toxoplasmosis and death in children and mothers infected during pregnancy. In some areas of the world (e.g., Asia) over 90% of the population may be infected with 3–4% with retinal involvement and visual loss. Control of the disease in humans will require development of a vaccine either for humans or for the animals from which humans predominantly acquire this disease (i.e., cats, pigs). Development of live, attenuated, or killed vaccines for pathogens are dependent upon development of large scale production techniques for growth of these organisms. *T. gondii* is normally grown by intraperitoneal inoculation of mice. This is far too expensive a technique to grow large numbers of organisms and also requires the use of laboratory animals. While *T. gondii* has been isolated from specimens in fibroblast cell lines, these cell lines grow in adherent monolayers and therefore do not allow accumulation of large parasite densities. No large scale production technique for growth of tachyzoites, the tissue destructive form of *T. gondii*, has been performed as yet.

In the patent literature, there are several references which disclose immunization procedures involving *Toxoplasma gondii*. In U.S. Pat. No. 4,473,549 (Frenkel et al.), a method is disclosed for immunizing man and animals against toxoplasmosis which involves production and subcutaneous administration of a live, low-virulent form of *T. gondii*. U.S. Pat. No. 4,473,548 (Frenkel et al.) discloses a method of immunizing cats against shedding of Toxoplasma oocytes which involves treatment with an agent such as monensin or salinomycin which prevents such shedding while allowing immunization to the parasite. U.S. Pat. No. 4,480,043 (Trouyez) discloses a process for preparing toxoplasmas to be used for the diagnosis of toxoplasmosis involving inoculation of mice with a mixture of toxoplasmas and sarcomatous cells. Finally, U.S. Pat. No. 4,564,592 (Gaafar et al.) discloses production of a "Toxoplasma factor" believed to be responsible for pathologic conditions observed in toxoplasmosis. This patent discloses producing this toxofactor by injecting *T. gondii* intraperitoneally in mice, and subsequently recovering the factor, which is usable in vaccines, from the culture medium. None of these patents disclose a method for generating large-scale production of Toxoplasma parasites for use in vaccines and antibody detection.

SUMMARY OF THE INVENTION

A method for producing large-scale growth of tachyzoites, the tissue-destructive form of *Toxoplasma gondii*, is provided which comprises inoculating a non-adherent human monocytoid lymphoma with *T. gondii* tachyzoites, and maintaining the cell line in suitable tissue culture media until large numbers of *T. gondii* tachyzoites are present. Once the tachyzoites are produced in this way, they can further be used in vaccines and in rapid antibody detection tests and test kits. The method of the present invention improves over the prior art in that it can produce large quantities of *T. gondii* antigen in relatively short time periods, and these antigens can be prepared without the use of laboratory animals.

BRIEF DESCRIPTION OF THE FIGURES

FIG. 1 is a photomicrograph showing non-adherent monocytoid lymphoma cells infected with *T. gondii tachyzoites*.

FIG. 2 is an electron micrograph showing twelve tachyzoites in a single infected non-adherent cell.

DETAILED DESCRIPTION OF THE INVENTION

According to the present invention, there is provided a method for producing large scale growth of tachyzoites, the tissue-destructive form of Toxoplasma microorganisms, comprising inoculating with tachyzoites a non-adherent human monocytoid cell line of lymphoid lineage, followed by the culturing of the cell line. When these non-adherent monocytoid lymphoma cell lines are inoculated with Toxoplasma microorganisms, such as *Toxoplasma gondii*, and maintained in a suitable tissue culture media capable of supporting growth of these microorganisms, rapid production of Toxoplasma tachyzoites can be achieved on the order of 1 million microorganisms per ml of tissue culture media used. By suitable tissue culture media is meant a tissue culture fluid in which the inoculated cell lines themselves can be maintained while the microorganisms are grown.

Numerous non-adherent cell lines from humans and animals have been evaluated with respect to the maximization of Toxoplasma growth in vitro, and it appears that monocytoid lymphoma cell lines provide maximum growth for these organisms. In particular, a clone of U 937, a monocytoid histiocytic lymphoma cell line has been observe to support large scale production of *Toxoplasm gondii* when maintained in a suitable growth medium. The U937 cell line has been deposited in the American Type Culture Collection, and has been accorded accession number ATCC CRL 1593. Other tests are being conducted on similar cell lines, and it appears that other non-adherent cell lines, such as B cells and other monocytoid lineages, support rapid proliferation of Toxoplasma microorganisms.

In order to achieve the large scale production of tachyzoites in a particular non-adherent cell line, it is necessary that a tissue culture solution be provided which supports the rapid growth of the microorganisms yet at the same time can maintain the viability of the cell line. It has been discovered that a medium consisting primarily of RPMI 1640 and fetal calf serum is suitable for maintaining the cell line while rapid growth of *Toxoplasma gondii* or other similar microorganism occurs. This medium, known as RPMI 1640-FCS is comprised of the following ingredients:

(1) RPMI 1640: 80–85%
(2) Heat-inactivated Fetal Calf Serum: 16–20%
(3) Hepes Buffer (1-molar): 0.1–3%
(4) L-glutamine (200 millimolar): 0.1–3%
(5) Sodium pyruvate (1 micromolar): 0.1–3%

The final percentage of Fetal Calf Serum in the media should be about 16%, as this is the crucial ingredient in maintaining maximal growth of the cell line and the Toxoplasma tachyzoites. RPMI 1640 is a product of Grand Island Biological Company, Grand Island, N.Y., and contains the following ingredients (mg/L):

| | |
|---|---|
| Ca(NO$_3$)$_2$4H$_2$O (100) | L-methionine (15) |
| KCl (400) | L-phenylalanine (15) |
| MgSO$_4$ (48-84) | L-proline (20) |
| NaCl (6000) | L-serine (30) |
| Na$_2$HPO$_4$ (800) | L-threonine (20) |
| glucose (2000) | L-tryptophane (5) |
| glutathione (red) (1) | L-tyrosine (28.94, Na salt) |
| L-arginine (free base) (200) | L-valine (20) |
| L-asparagine (50) | biotin (.20) |
| L-aspartic acid (20) | D-Ca pantothenate (.25) |
| L-cystine (65.15, 2 HCl) | choline Cl (3) |
| L-glutamic acid (20) | folic acid (1) |
| L-glutamine (300) | i-inositol (35) |
| glycine (10) | nicotinamide (1) |
| L-histidine (free base) (15) | p-aminobenzoic acid (1) |
| L-hydroxyproline (20) | pyridoxine HCL (1) |
| L-isoleucine (allo free) (50) | riboflavin (20) |
| L-leucine (met-free) (50) | thiamine (1) |
| L-lysine HCl (40) | vitamin B12 (.005) |

The large scale production of microorganisms provided by the method of the present invention is preferable carried out by growing a non-adherent cell line in 100 ml of RPMI 1640-FCS in a flask or other container for a period of about 2 to 3 days, under temperatures ranging from about 36° C. to 37° C. After the particular cell line is established, the flasks are inoculated with the desired Toxoplasma microorganism, such as *Toxoplasma gondii*, and kept at a temperature of around 37° C. for a period of about 7 days. Under these conditions, a total number of about 1 million Toxoplasma tachyzoites per ml of tissue culture fluid can be produced. Growth of tachyzoites has been maintained in these tissue cultures for over 3 months. After large numbers of Toxoplasma tachyzoites or other microorganisms have been produced by this process, it is then possible to prepare vaccines or antibody detection tests using these microorganisms.

According to the present invention, vaccines are also provided which comprise killed or irradiated Toxoplasma tachyzoites obtained using the culturing method described above. In order to obtain a vaccine with whole, killed Toxoplasmal tachyzoites, a non-adherent cell line as described above is inoculated with *T. gondii* from a stock culture and allowed to grow in RPMI 1640-fetal calf serum for around 7 days. After proliferation of the *T. gondii* tachyzoites in the culture media, cellular debris is separated from the tachyzoites by differential centrifugation. At this point, the organisms are washed several times with RPMI 1640 solution, and then are placed into hypotonic solution in order to kill the organisms. Tests showed that dye exclusion was absent after 7 days of hypotonic treatment, indicating complete inactivity of the organisms. A vaccine was then prepared employing the killed organisms and alum, which was added to the solution to enhance immunogenicity. A second vaccine has been prepared using irradiated *T. gondii* tachyzoites. Both of these vaccines should contain an amount of the killed or irradiated tachyzoites sufficient to create an immunological response in the recipient.

The development of these two vaccines against diseases caused by Toxoplasma organisms has not before been possible due to the lack of viable numbers of these organisms. The ability to grow large numbers of Toxoplasma tachyzoites using the tissue culturing techniques of the present invention thus has allowed for the production of these vaccines.

It is contemplated that the vaccines prepared in accordance with the present invention will be administered parenterally, preferably by intramuscular or intravenous injection. It is also intended that these vaccines will be most effectively employed by administering them to the animals from which humans predominantly acquire this disease, particularly cats and pigs. Through a vaccination program of these animals using the vaccines of the present invention, it will be much more likely that diseases caused by Toxoplasma microorganisms in humans will effectively be controlled.

Another feature of the present invention is that rapid tests for antibody detection to *T. gondii* are now made possible by virtue of the large scale growth of these organisms provided by the above culturing methods. In the past, serologic studies conventionally performed with respect to the diagnosis of *T. gondii* infection, such as the indirect hemagglutination assay, have been time consuming (>6 hours), and require both expensive equipment and/or highly skilled technicians. Utilizing the Toxoplasma tachyzoites as grown in the method described above, rapid tests (2-4 hours) have been developed for antibody detection which require no expensive equipment or skilled technicians. These antibody assays are the soft plate ELISA test and the rapid dot blot technique (RDBT), and the tests to detect the IgG antibody to Toxoplasmal tachyzoites as follows:

I. 2 hour soft-plate ELISA test:

Plates are prepared using Toxoplasmal tachyzoites grown as described above. Whole killed tachyzoites are fixed to Dynatech soft mic-2000 ELISA plates which are then blocked with filler, washed with phosphate buffered saline, and stored at around 4° C. until desired for use.

To assay for IgG antibody detection, 25 microliters (μl) of serial dilutions of positive and negative control sera and the specimens to be tested are added to the well of the plates prepared above and incubated at room temperature for about 1 hour. The sera are then aspirated, and the plates are washed several times with phosphate buffered saline (PBS). At this point, 25 μl of goat or other anti-human alkaline phosphate labelled conjugate is added to each well for at least 45 minutes, after which the plates are aspirated and washed again with PBS. The plates can then be developed by adding about 50 ml of a substrate/buffer solution. A yellow reaction will occur in a positive dilution, and this can be quantitated by a reading on a Dynatech ELISA instrument.

II. Rapid 4 hour dot blot technique (RDBT)

The Toxoplasmal tachyzoites grown in tissue culture as described above are fixed as whole tachyzoites on nitrocellulose discs and then blocked with filler. The discs can then be stored for use until desired, preferably at a temperature of about 4° C.

When an assay for detection of the IgG antibody to a Toxoplasmal parasite is desired, serial dilutions of positive and negative control sera along with the specimens to be tested are added to each disc in a 96 plastic plate or 24 well plastic disk and incubated at room temperature for at least 90 minutes. The sera are then aspirated, and the discs washed at least once with phosphate buffer saline (PBS). Goat anti-human IgG antibody labelled with alkaline phosphatase is added to each well for at least 90 minutes, then the label is aspirated, and the discs washed three times with PBS. A tris buffer is then added to each disc, followed by addition of a napthol salt-fast red TR dye. This dye produces a bright red reaction on any disc in which antigen-antibody reactions have occurred.

Using these two tests described above, one can rapidly, efficiently, and without highly skilled technical help, be able to diagnose the presence of antibodies to *T. gondii* or other harmful microorganisms. The above plates or discs can be prepared and put into kits by which convenient and inexpensive testing for antibodies to various microorganisms, particularly toxoplasmal parasites, can be accomplished.

Both the assay tests and the vaccines described above are possible because of the development of the large scale production of tachyzoites as provided in the present invention. The utilization of the tissue culture techniques disclosed herein allow for the preparation of large quantities of antigens inexpensively, and without the need to use laboratory animals. Although these techniques are specifically described for Toxoplasma parasites it is quite probable that such techniques can be used to allow large scale production of many other microorganisms as well.

The following example is presented as illustrative of the present invention and should not be construed as limiting in any way:

EXAMPLE

A vaccine was prepared in accordance with the present invention by first obtaining large scale production of the microorganism Toxoplasma gondii. The large scale growth of *T. gondii* was obtained by first growing a non-adherent monocytoid lymphoma cell line known as U 937 in the following culture medium (known as RPMI 1640-FCS):

RPMI 1640: 500 ml
Heat-inactivated Fetal Calf Serum: 100 ml
Hepes buffer (1 molar): 5 ml
L-glutamine (200 millimolar): 5 ml
Sodium pyruvate (1 micromolar): 5 ml The non-adherent cell line was grown in a flask containing 100 ml of the RPMI 1640-FCS solution for a period of 3 days at a temperature of 37° C. After this cell line was established, the flask was inoculated with *Toxoplasma gondii* tachyzoites. These organisms were then cultured at a temperature of 37° C. for a period of seven days. These culturing techniques resulted in large scale growth of *T. gondii* on the order of roughly 1 million *T. gondii* tachyzoites per ml of tissue culture fluid.

These results are evidenced by micrographs of the cultured material, as presented in FIGS. 1 and 2. FIG. 1 is a photomicrograph which shows numerous infected U 937 cells infected with up to 30 tachyzoites(see arrows). FIG. 2 is an electron micrograph which shows 12 tachyzoites in phagosomes (see arrows) in a single infected cell. One million cells infected at this magnitude thus would result in approximately 12 million tachyzoites.

A vaccine containing whole, killed *Toxoplasma gondii* tachyzoites was prepared using the tachyzoites obtained in the culturing procedure described above. After *T. gondii* tachyzoites had proliferated in the above culture media, cellular debris was separated from the tachyzoites by differential centrifugataion. At this point, the organisms were washed several times with RPMI 1640 solution, and were then placed into hypotonic solution in order to kill the organisms. Tests showed that dye exclusion was absent after 7 days of hypotonic treatment, indicative of complete inactivity of the organisms. A vaccine was then prepared employing the killed organisms and alum, which was added to the vaccine in order to enhance immunogenicity.

What is claimed is:

1. A method of the large-scale production of Toxoplasma tachygzoites for use in vaccines and antibody detection procedures, comprising the steps of inoculating with Toxoplasma tachyzoites a clone of cell line U 937 (ATCC CRL 1593) and maintaining the clone in a tissue culture medium capable of supporting the growth of the inoculated Toxoplasma microorganisms in addition to maintaining the clone, wherein the tissue culture medium consists essentially of RPMI 1640 and fetal calf serum.

2. A method according to claim 2, wherein Toxoplasma microorganisms are produced at a rate of at least about one million microorganisms per ml of tissue culture medium per week.

3. A vaccine comprising killed or irradiated Toxoplasma tachyzoites produced by the method of claim 1, where the tachyzoites are present in the vaccine in an amount sufficient to create an immunological response.

4. A vaccine according to claim 3, wherein the Toxoplasma tachyzoites are irradiated tachyzoites.

5. A vaccine according to claim 3, wherein the Toxoplasma tachyzoites are *T. gondii* tachyzoites.

6. A method according to claim 1, wherein the Toxoplasma tachyzoites are *T. gondii* tachyzoites.

7. A method according to claim 1, wherein fetal calf serum is present in the tissue culture medium in a concentration of about 16%.

* * * * *